US00PP26276P2

(12) United States Plant Patent
Trewavas

(10) Patent No.: US PP26,276 P2
(45) Date of Patent: Dec. 29, 2015

(54) ***NANDINA* PLANT NAMED 'LITTLE FLICK'**

(50) Latin Name: *Nandina domestica*
Varietal Denomination: Little Flick

(71) Applicant: Peter Trewavas, Motueka (NZ)

(72) Inventor: Peter Trewavas, Motueka (NZ)

( * ) Notice: Subject to any disclaimer, the term of this patent is extended or adjusted under 35 U.S.C. 154(b) by 124 days.

(21) Appl. No.: 13/987,047

(22) Filed: Jun. 28, 2013

(51) Int. Cl.
*A01H 5/00* (2006.01)

(52) U.S. Cl.
USPC ..... Plt./235

(58) Field of Classification Search
USPC ..... Plt./235
See application file for complete search history.

(56) References Cited

PUBLICATIONS http://www.thirkettlenurseries.co.nz/catalogue/plants.php-?pageNum_rs_plant=9&totalRows_rs_plant=290 &rs=rscategorylist&stype=categorylist&&value1=8 2010.*

* cited by examiner

*Primary Examiner* — Kent L Bell

(57) ABSTRACT

A new cultivar of *Nandina* plant named 'Little Flick' that is characterized by a dense compact habit, red upper leaves and green lower leaves.

1 Drawing Sheet

Botanical classification: *Nandina domestica.*
Variety denomination: 'Little Flick'.

BACKGROUND OF THE INVENTION

The present invention relates to a new and distinct cultivar of *Nandina* plant botanically known as *Nandina domestica* and hereinafter referred to by the cultivar name 'Little Flick'.

The new cultivar was discovered in 2008 as a naturally occurring whole plant mutation in a population of *Nandina domestica* 'Gulf Stream' (U.S. Plant Pat. No. 5,656) plants. 'Little Flick' was discovered as a single plant in a greenhouse in a cultivated area of Motueka, New Zealand.

Asexual reproduction of the new cultivar 'Little Flick' by tissue culture was first performed in 2009 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Nandina* cultivar 'Little Flick'. These traits in combination distinguish 'Little Flick' as a new and distinct cultivar.

1. *Nandina* 'Little Flick' exhibits a dense compact habit.
2. *Nandina* 'Little Flick' exhibits red upper leaves and green lower leaves.

The closest comparison cultivar is the parent plant 'Gulf Stream'. 'Little Flick' differs from 'Gulf Stream' in having a smaller overall size and in having red colored upper leaves and green colored lower leaves. In comparison, the leaves of 'Gulf Stream' are yellow-green in color.

BRIEF DESCRIPTION OF THE DRAWING

The accompanying photograph illustrates the distinguishing traits of *Nandina* 'Little Flick'. The plant in the photograph shows an overall view of a 24 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Nandina* cultivar named 'Little Flick'. Data was collected in Motueka, New Zealand from 24 month old greenhouse grown plants. The time of year was Autumn and the average temperature was 15 to 22° Centigrade during the day and 6 to 14° Centigrade at night. Color determinations are in accordance with The Royal Horticultural Society Colour Chart 2001 edition, except where general color terms of ordinary dictionary significance are used. The growing requirements are similar to the species. 'Little Flick' has not been tested under all possible conditions and phenotypic differences may be observed with variations in environmental, climatic, and cultural conditions, however, without any variance in genotype.

Botanical classification: *Nandina domestica* 'Little Flick'.
Use: Ornamental Perennial.
Parentage: 'Little Flick' is a naturally occurring whole plant mutation of *Nandina domestica* 'Gulf Stream'.
Habit: Compact and bushy.
Vigor: Vigorous.
Plant type: Shrub.
Plant shape: Upright, rounded.
Overall height: 50 cm.
Overall width: 60 cm.
Root system: Thick and fibrous.

*Hardiness.*—USDA Zone 6.
*Propagation method.*—Tissue culture, micro-propagation of shoots.
*Time to develop roots.*—6 to 8 weeks to root cuttings.
*Crop time.*—12 months.

Stem:

*Stem dimensions.*—Basal stems 1.4 cm. in diameter and 32 cm. in length.

*Stem color.*—177B with stripes 200A.

*Stem surface.*—Coriaceous.

*Stem strength.*—Strong and rigid.

*Internode surface.*—Glabrous.

*Internode color.*—146A.

*Internode dimensions.*—5 mm in diameter and 25 mm. in length.

Foliage:

*Type.*—Evergreen.

*Arrangement.*—Alternate.

*Leaf division.*—Odd tripinnately compound.

*Attachment.*—Petiolate.

*Leaf dimensions.*—23 to 28 cm. in length and 15 to 21 cm. in width.

*Petiole dimensions.*—12 mm. in length and 1.1 mm. in diameter.

*Petiole color.*—147A.

*Petiole surface.*—Glabrous.

*Leaflet shape.*—Lanceolate.

*Leaflet base.*—Attenuate.

*Leaflet apex.*—Apiculate.

*Leaflet margin.*—Entire.

*Leaflet dimensions.*—5 to 7.5 cm. in length and 1.0 to 1.8 cm. in width.

*Leaflet texture.*—Glabrous on both surfaces.

*Leaflet color* (*lower surface*).—Lower leaflets are 147B and upper leaflets are 187B.

*Leaflet color* (*upper surface*).—Lower leaflets are 147A and upper leaflets are 187A.

*Vein pattern.*—Pinnate.

*Vein color* (*lower surface*).—Lower leaflets 147B, upper leaflets 187B.

*Vein color* (*upper surface*).—Lower leaflets 147A, upper leaflets 187A.

*Petiolule dimensions.*—14 to 24 mm. in length and 0.9 to 1.0 mm. in diameter.

*Petiolule color.*—147A.

*Petiolule surface.*—Glabrous.

*Flowers.*—No flowers have been produced by 'Little Flick' to date.

Disease and pest resistance: Plants of the new *Nandina* have not been observed for disease or pest resistance.

It is claimed:

1. A new and distinct variety of *Nandina* plant named 'Little Flick' as described and illustrated.

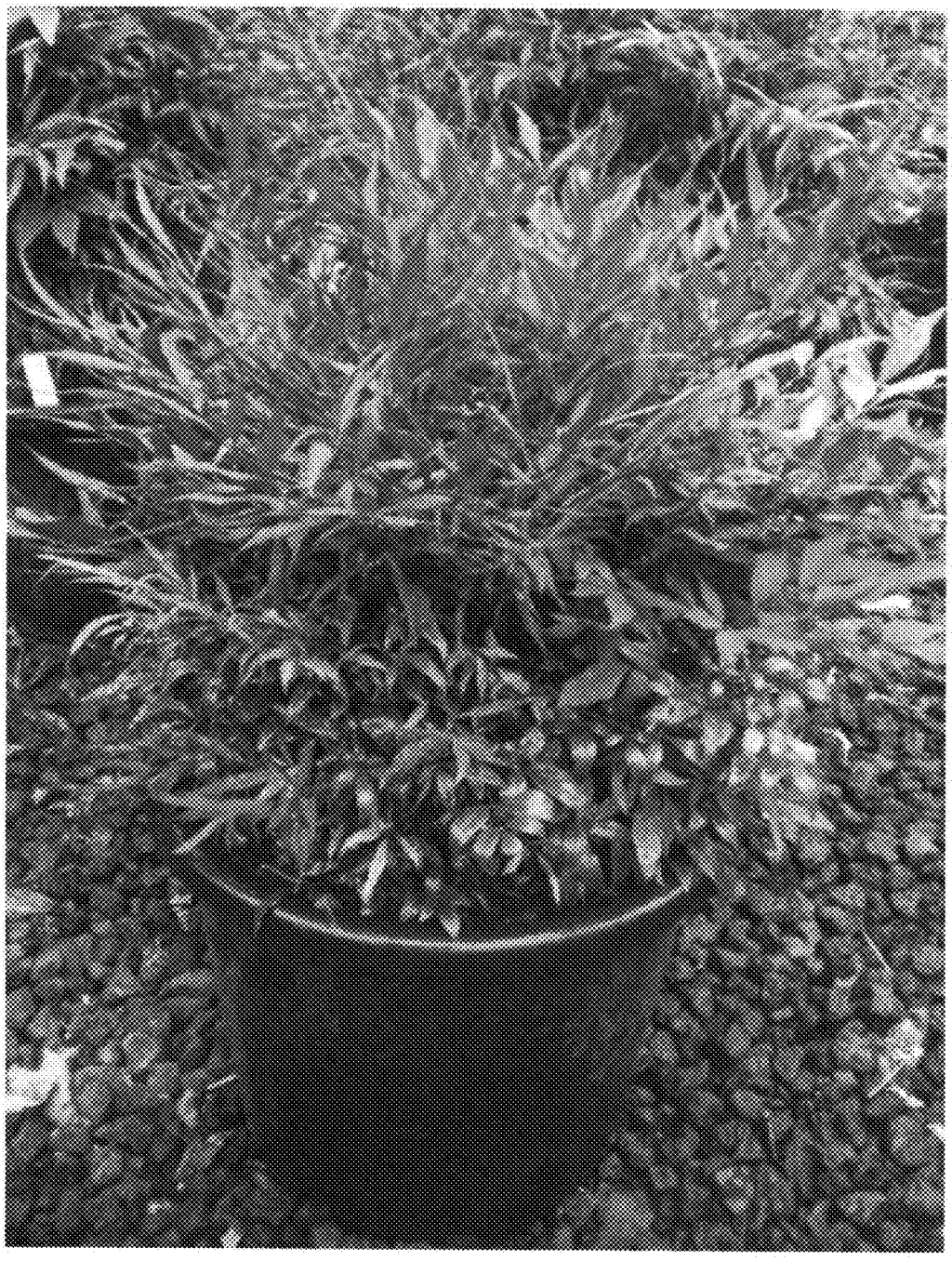

* * * * *